United States Patent
Gebhardt

(10) Patent No.: US 6,248,778 B1
(45) Date of Patent: Jun. 19, 2001

(54) ANTICHOLESTATIC EFFECT OF LUTEOLIN

(75) Inventor: Rolf Gebhardt, Leipzig (DE)

(73) Assignee: Sertürner Arzneimittel GmbH, Gutersloh (DE)

( * ) Notice: Subject to any disclaimer, the term of this patent is extended or adjusted under 35 U.S.C. 154(b) by 0 days.

(21) Appl. No.: 09/492,004

(22) Filed: Jan. 27, 2000

(30) Foreign Application Priority Data

Jan. 25, 1999 (DE) .............................................. 199 02 773

(51) Int. Cl.$^7$ .................................................. A61K 3/35
(52) U.S. Cl. .................................................. 514/457
(58) Field of Search .............................................. 514/457

(56) References Cited

U.S. PATENT DOCUMENTS

| | | | |
|---|---|---|---|
| 5,863,550 | * 1/1999 | Maeda et al. | 424/423 |
| 5,952,391 | * 9/1999 | Gers-Barlag et al. | 514/685 |
| 6,020,310 | * 5/2000 | Sokol | 514/458 |
| 6,025,387 | * 2/2000 | Yoo et al. | 514/457 |

OTHER PUBLICATIONS

Gebhardt, J. Pharmacol. & Exp. Therap., vol. 286, pp. 122–1128, 1998.*

Yugarani er al, Lipids, vol. 27, #3, pp. 181–186 (abstract), Mar. 1997.*

* cited by examiner

*Primary Examiner*—James H. Reamer
(74) *Attorney, Agent, or Firm*—Arent Fox Kintner Plotkin & Kahn, PLLC

(57) ABSTRACT

The invention relates to a drug for treating or preventing intrahepatic cholestasis, which is characterized by containing as active agent at least one compound with the general formula I,

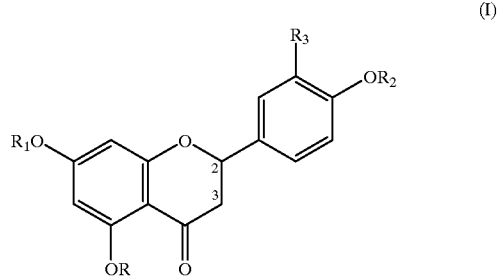

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof.

12 Claims, No Drawings

ANTICHOLESTATIC EFFECT OF LUTEOLIN

SPECIFICATION

The invention relates to a drug for treating or preventing intrahepatic cholestasis.

Cholestasis is a syndrome caused by dysfunctional bile flow. A distinction is made between extrahepatic and intrahepatic cholestasis. Extrahepatic cholestasis is usually caused by a bile duct stone or a pancreatic carcinoma. In the case of intrahepatic cholestasis there is congestion in the bile ducts. The most common causes of intrahepatic cholestasis are viral and other hepatitides, drugs used to treat cancer, for example, and alcohol-induced liver damage. Less common causes are primary biliary cirrhosis, cholestasis during pregnancy, and other diseases.

Extract from the leaves of artichokes (Cyanara scolymus L.) is known for its choleretic effect in the case of dyspeptic complaints. Genuine choleretic agents, which artichoke extract is considered to be, lead to an increase in the quantity of bile acids, whereas non-genuine choleretic agents lead to an increase in the volume of bile fluid. In addition to its choleretic effect, artichoke extract is described in the literature as having an anticholestatic effect (Ärzte-Ztg., 15th vol., 1996, page 16). Until now, however, it was not known which active agent is responsible for the anticholestatic effect.

The object of this invention was thus to provide a drug which contains an active agent with an anticholestatic effect of defined efficacy.

This object was established according to the invention by means of a drug for treating or preventing intrahepatic cholestasis, which is characterized by containing as active agent at least one compound of the general formula I,

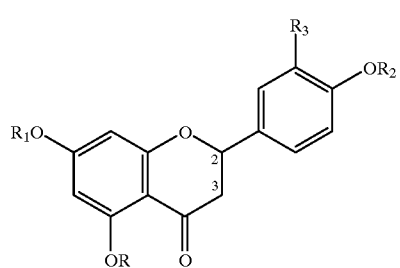

(I)

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof.

It was found that the compounds of formula I have an anticholestatic effect and are therefore suitable for treating intrahepatic cholestasis. An intrahepatic change in the bile ducts can be prevented or reversed with compounds of formula I, so that prophylactic treatment to prevent intrahepatic cholestasis is also possible.

With the knowledge that compounds of formula I have an anticholestatic effect, it is possible to manufacture a standardized drug with a predetermined and defined effective dose. With the drug disclosed, moreover, it is possible to achieve a fast and accurately targeted effect.

Extracts of artichoke, especially dry extracts of artichoke leaves such as are commercially available from Sertürner Arzneimittel under the name HEPAR-SL® forte, contain numerous compounds which could be potential active agents. Until now, it was not possible to attribute the anticholestatic effect of the extract to any particular one of the many compounds contained therein. It was thus difficult to manufacture a standardized drug from the artichoke extract.

It has now been found that it is compounds of formula I that show an anticholestatic effect. Free compounds with the formula I, especially luteolin, are present, if at all, in only small amounts of <0.08 wt %, expressed in terms of the overall extract, in artichoke extract. Moreover, there is no indication in the prior art that of all possible compounds precisely those of formula I might show an anticholestatic effect.

Known components of artichoke extract are caffeic acid, chlorogenic acid, cynarine (1,5-di-O-caffeoyl-chinic acid), 1,3-di-O-caffeoyl-chinic acid, scolymoside and cynaroside (luteolin-7-O-glucoside). Cynaroside (luteolin-7-O-glucoside) is cleaved in the gastrointestinal tract, thus liberating luteolin. However, cynaroside is also found in many other plants for which no such anticholestatic effect has been reported. Cynaroside itself shows no anticholestatic effect.

Anticholestatic and choleretic agents work quite differently. A condition of cholestasis which is frequently used as a model and is triggered by taurolithocholate causes an easily detectable membrane change. Known choleretics are generally not able to prevent or reverse this membrane modification (Layden et al., Gastroenterology 50 (1977), 2305 to 2312). Dehydrocholic acid, for example, which is known to have a choleretic effect, had no effect on a taurolithocholate-initiated cholestasis. Thus the use of compounds which are effective as choleretics are generally not suitable for treating cholestasis.

In compounds of the general formula I in which R, $R_1$ and/or $R_2$ are H, there is a hydroxyl group at the corresponding positions 5, 7 and/or 4' of the flavone or flavanone basic structure. For the case that R, $R_1$ and/or $R_2$ stand for an $C_{1-2}$-alkyl group, especially a methyl or ethyl group with methyl being particularly preferred, there is an ether grouping at the corresponding positions. If R, $R_1$ and/or $R_2$ stand for a $C_{1-3}$-acyl group, there is an ester group at the corresponding positions. Preferred acyl groupings are a formyl radical, an acyl radical, a propionyl radical and a lactyl radical. Compounds in which there is a single bond between positions 2 and 3 have the basic structure of flavanone

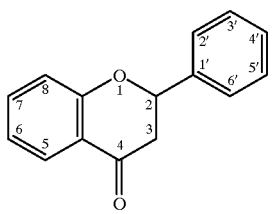

while compounds in which there is a double bond between positions 2 and 3 have the basic structure of flavone.

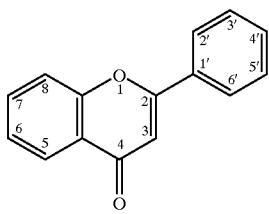

Physiologically acceptable salts of a compound of formula I comprise all physiologically harmless, salt-like compounds which include the compound of formula I in ionic form, together with a counterion. Acid-addition salts constitute particularly good examples of such salts.

It is preferable if the drug of the invention contains a compound with the general formula I, in which R, $R_1$ and/or $R_2$=H. Compounds of this kind, in which there are free -OH groups, especially at positions 5 (corresponds to radical R) and/or 7 (corresponds to radical $R_1$), were found to exhibit particularly high efficacy.

It is also beneficial if the drug of the invention contains a compound with the general formula I, in which $R_2$ is an —OH group.

An especially high level of efficacy was found in the case of luteolin (R=H, $R_1$=H, $R_2$=H, $R_3$=OH, there being a double bond between positions 2 and 3), apigenin (R=H, $R_1$=H, $R_2$=H, $R_3$=H, there being a double bond between positions 2 and 3), and naringenin (R=H, $R_1$=H, $R_2$=H, $R_3$=H, there being a single bond between positions 2 and 3). The greatest preference is given to luteolin. The compounds luteolin-7-O-glucoside, 3', 4'-hydroxyflavone, genistein and daidzein showed no anticholestatic effect.

The drug of the invention preferably contains compounds of formula 1 in a quantity of >0,1 wt %, more preferably >1 wt %, more preferably still >10 wt % and, most preferably of all, >20 wt %. However, it is also possible to make up drugs which have an even higher content of at least one compound of formula I, in particular >50 wt % expressed in terms of the overall weight of the drug.

To effectively treat or prevent an intrahepatic cholestasis, patients are generally given a daily dose of 10 to 1 000 mg of a compound with the general formula I. It is of advantage to administer a daily dose of at least 20 mg, preferably at least 50 mg and best of all at least 100 mg of a compound with the general formula I, and, at the most, a daily dose of up to 750 mg, preferably up to 500 mg and best of all up to 300 mg.

If desired, the drug of the invention can be formulated with physiologically acceptable auxiliaries and carriers. Such auxiliaries must be physiologically harmless and must not impair the efficacy of the active agents. Suitable auxiliaries are known to those versed in the art, and include, for example, fillers, binders and lubricants, for example microcrystalline cellulose, amylose, lactose, mannitol, talcum, magnesium stearate, starch, microdispersed magnesium oxide, silicon dioxide, sodium carboxymethyl starch, polyvidone, macrogol etc.

The drug disclosed in the invention can be produced in all administrable drug forms known to those versed in the art. It is preferably produced in a formulation suitable for oral administration, in particular in solid form. Examples of such solid drug forms include capsules, tablets, granulates, sugar-coated tablets, film-coated tablets and the like. Preference is given to formulations where the active agent is released in the gastrointestinal tract, and not before.

The drug disclosed in the invention can contain a single effective compound of general formula I, or several such effective compounds. It can be a drug in which at least one compound with the general formula I constitutes the only active agent, i.e., apart from the compounds of general formula I, the drug contains only inert auxiliaries and carriers. For a drug of this kind, use can be made of active agents isolated from plant extracts, or of chemically synthesized compounds. The isolation of corresponding flavone and flavanone derivatives such as luteolin from plant extracts has been described comprehensively in the literature (cf. eg, Pharmacia 21 (39) (1972) 37). The chemical synthesis of compounds with the general formula I can likewise be conducted according to methods which are known per se and have been documented (cf. eg, J. Chem. Soc. 1939, 91). There are also numerous compounds with the formula I which are commercially available.

It is also possible to produce a drug which, besides the compound with the general formula 1, also contains other active agents. To this end, an isolated or chemically synthesized compound of formula I can be mixed with other active agents and, if required, auxiliaries or carriers. Another alternative is to use a plant extract, for example an artichoke extract, which contains not only compounds with the general formula I but other active agents as well. If a natural extract is used, a drug as disclosed in the invention is produced by enriching the content of formula 1 compounds contained in a conventional extract, so that in terms of its overall weight, the extract contains >0.1 wt %, preferably >1 wt %, even more preferably >10 wt %, and best of all >20 wt % of compounds with the formula 1. The extract can be enriched in this way by choosing the extraction conditions such that the proportion of compounds with the general formula I contained in the extract is as high as possible. However, it is also possible to increase the concentration of active agent in a commercially available extract by adding to it at least one compound with the general formula I.

Yet another way of obtaining an extract enriched with active agent is to increase the content of free formula I compounds in a commercial extract, for example an artichoke extract, by breaking down glycosylated formula I compounds prior to use of the extract. This can be done, for example, by means of heat, pH influence, or enzymatically. The luteolin content in an artichoke extract, for example, can be increased prior to administration by breaking down the cyanaroside present in the artichoke extract to free luteolin. Ester- and ether-substituted compounds of the general formula I can be converted analogously to the active-agent form, for example by means of corresponding cleavage enzymes.

The invention also relates to a method of producing a drug for the treatment or prevention of intrahepatic cholestasis, which is characterized in that at least one compound with the general formula I,

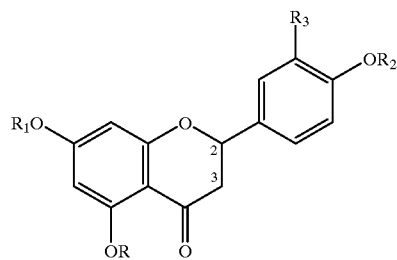

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof, is incorporated as active agent—optionally together with standard pharmacological additives—into a physiologically administrable formulation.

The invention relates further to the use of at least one compound of formula 1 as a drug for the treatment or prevention of intrahepatic cholestasis, which is characterized in that at least one compound with the general formula I,

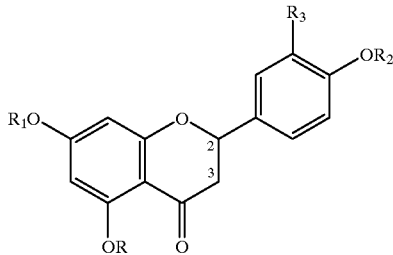

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof, is administered as active agent—optionally together with standard pharmacological additives—in a dosage of 0.01 to 1 g per day.

The invention is explained in more detail by means of the following example.

EXAMPLE 1

Prevention of a taurolithocholate-induced transformation of canalicular membranes In live rats, taurolithocholate induces a severe cholestasis which is connected with the transformation of the bile canaliculi into bizarrely structured lamellar membrane formations. The induction of intrahepatic cholestasis with lithocholic acid and sodium taurolithocholate in animal experiments is described in detail in the literature (Javift, N. B., Nature 210, (1966), 1262–1263; King, J. E. et al., J. Clin. Invest. 50, (1971) 2305–2312; Layden et al., Gastroenterology 73 (1977), 120–128; Mockel et al., Am. J. Physiol., 269 (1995), G73–G84). In addition to a canalicular dilation, they induced bizarre lamellar deformations of the ultrastructure of the bile canaliculi. Such deformations are characteristic of this kind of cholestasis (Miyai et al., Lab. Invest. 32 (1975), 527–535; Kakis et al., Lab. Invest. 43, (1980) 73–81). It was recently shown that taurolithocholate, when added to primary cultures of rat hepatocytes, formed similar deformations in vitro. The in vitro deformations cannot be distinguished from those formed in vivo (Jung et al., Eur. J. Cell Biol. 29, (1982) 77–82; Thibault et al., J. Hepatol. 19 (1993) 367–376). For the experiments, therefore, the transformation of newly formed bile canaliculi by taurolithocholate was triggered as described (Jung et al., Eur. J. Cell Biol. 29 (1982) 77–82) in primary cultures of rat hepatocytes.

Parenchymal liver cells were isolated from male Sprague-Dawley rats (220 to 280 g) and cultivated for 2 days in a serum-free Williams Medium E as described (Gebhardt et al., Cell Biol. Toxicol. 6 (1990) 369–372; Gebhardt, Toxicol. Appl. Pharmacol. 144 (1997), 270–286). For treating the cultured hepatocytes with taurolithocholate, a 10 mM stock solution of this bile salt was prepared with ethanol and diluted with Williams Medium E to give a final concentration of 0.1 mM. Hepatocytes cultured for 1 to 2 days were treated with this taurolithocholate-containing medium for 3 hours in order to induce maximum changes in the bile canaliculi (Jung et al., Eur. J. Cell Biol. 29 (1982), 77–82). In primary cultures of rat hepatocytes, taurolithocholate (0.1 mM) induces pronounced transformation of the canalicular membranes to bizarrely structured formations within 3 hours. The normal canalicular membrane, which is covered with numerous microvilli, is transformed into bizarre lamellar structures which almost entirely fill the canaliculus. This process appears to be complete after 2 to 3 hours, and affected some 50 to 70% of the canaliculi on the second day of cultivation.

The membrane changes in the bile canaliculi were detected by means of electron microscopy performed on ultra-thin sections (cf. Gebhardt et al., Eur. J. Cell Biol. 29 (1982) 68–76). To prepare the sections, cultured cells were fixed for 30 to 45 minutes in situ with 2.5% glutaraldehyde in 0.1 M cacodylate buffer, pH 7.2, at 0° C. After being washed with cacodylate buffer, the cells were introduced at 46° C. into a 2% solution of agar, which was cut into small pieces and afterfixed in 1% $OSO_4$ in a cacodylate buffer. Following dehydration, the blocks were embedded in Epon 812. After staining, silver sections were examined with a Siemens 1a electron microscope.

To obtain a semi-quantitative estimate of the change in the canalicular membranes, the appearance of 100 bile canaliculi from two to three different experiments was examined. The canaliculi were classified as transformed if half or more of the canalicular surface was covered with bizarre lamellar structures.

The experiment described above was repeated, various active agents being added to the primary cultures of rat hepatocytes at the same time as the taurolithocholate. The addition of luteolin in a quantity of 28 mg together with the taurolithocholate resulted in complete inhibition of the lamellar transformation. Instead, the bile canaliculi retained their microvilli, even if in a somewhat reduced number, and were only slightly dilated. A similar effect was obtained by pre-incubating the cultures with luteolin. This shows that a possible adsorption of taurolithocholate on other components plays no role. Preferably, however, no more than 60 minutes should elapse between pre-incubation and the addition of taurolithocholate.

It was also found that protection against taurolithocholate-induced transformation was dependent on the dose.

The experiments were repeated with apigenin, an extract of Gentiana lutea, and the isoflavonoid genistein. Whereas apigenin had the same effect as luteolin, the Gentiana lutea extract and the isoflavonoid genistein had no effect.

The compounds of formula I are thus able to specifically inhibit the taurolithocholate-induced transformation of the canalicular membranes, and to show an anticholestatic effect. This effect is presumably brought about by way of protein kinase inhibition.

What is claimed is:

1. A drug for treating or preventing intrahepatic cholestasis,
wherein
at least one compound with the general formula I,

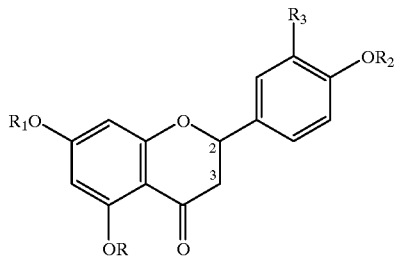

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof is contained as active agent.

2. The drug of claim 1,
wherein
a compound with the general formula I in which R, $R_1$ and $R_2$=H is contained.

3. The drug of claim 1,
wherein
a compound with the general formula I in which $R_3$=OH is contained.

4. The drug of claim 1,
wherein
compounds with the general formula I are contained in a quantity of >1 wt %.

5. The drug of claim 1,
wherein
compounds with the general formula I are contained in a quantity of ≧20 wt %.

6. A method of producing a drug for the treatment or prevention of intrahepatic cholestasis,
wherein
at least one compound with the general formula I,

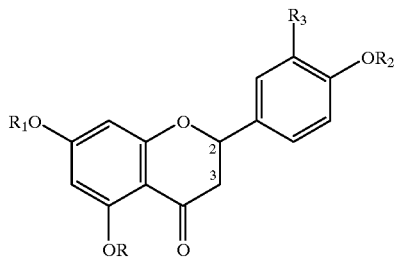

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof, is incorporated as active agent—optionally together with standard pharmacological additives—into a physiologically administrable formulation.

7. The method of claim 6,
wherein
a compound with the general formula I in which R, $R_1$ and $R_2$=H is contained in the formulation.

8. The method of claim 6,
wherein
a compound with the general formula I in which $R_3$=OH is contained in the formulation.

9. The method of claim 6,
wherein
the administrable formulation contains ≧1 wt % of compounds with the formula I.

10. The method of claim 6,
wherein
the administrable formulation contains ≧20 wt % of compounds with the formula I.

11. Use of at least one compound with the general formula I,

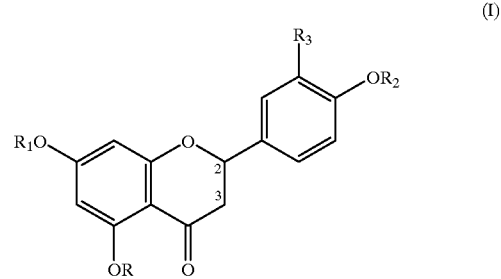

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof as active agent for the treatment or prevention of intrahepatic cholestasis.

12. A method of treating or preventing intrahepatic cholestasis,
wherein
at least one compound with the general formula I,

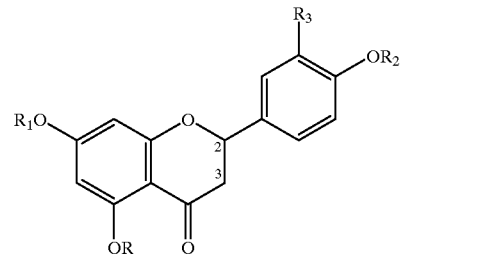

where R, $R_1$ and $R_2$ are independent of each other and can each =H, $C_{1-2}$-alkyl or $C_{1-3}$-acyl, $R_3$=H or $OR_4$ and $R_4$=H, $C_{1-2}$-alkyl or $C_{1-4}$-acyl, and there is a single or double bond between positions 2 and 3, or a physiologically acceptable salt thereof is administered as active agent—optionally together with standard pharmacological additives—in a dosage of 0.01 to 1 g per day.

* * * * *